US00PP23716P3

(12) United States Plant Patent
Scully et al.

(10) Patent No.: US PP23,716 P3
(45) Date of Patent: Jul. 2, 2013

(54) ZOYSIAGRASS PLANT NAMED 'BA-189'

(50) Latin Name: ***Zoysia japonica* Stued**
Varietal Denomination: BA-189

(75) Inventors: Brian T. Scully, Fernandina Beach, FL (US); Russell T. Nagata, Hilo, HI (US); Dorothy M. Sistrunk, Belle Glade, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 2406 days.

(21) Appl. No.: 11/174,308

(22) Filed: Jul. 5, 2005

(65) Prior Publication Data

US 2012/0324611 P1 Dec. 20, 2012

(51) Int. Cl.
*A01H 5/00* (2006.01)

(52) U.S. Cl.
USPC ..... Plt./390

(58) Field of Classification Search
USPC ..... Plt./390
See application file for complete search history.

*Primary Examiner* — Susan McCormick Ewoldt
(74) *Attorney, Agent, or Firm* — Jondle Plant Sciences Division of Swanson & Bratschun, L.L.C.

(57) ABSTRACT

A newly discovered, and asexually reproduced genotype of Zoysiagrass with a distinct set of foliar, floral and agronomic traits.

6 Drawing Sheets

Genus and species: *Zoysia japonica* Stued.
Variety denomination: 'BA-189'.

BACKGROUND OF THE INVENTION

This invention relates to a new and distinct genotype of Zoysiagrass of the genus and species *Zoysia japonica* Stued. It is described herein and designated as 'BA-189'. As used herein, 'BA-189' has the identical meaning as 'Ultimate *Zoysia*'. This invention was discovered and identified in Palm Beach County, Fla. as a distinctly different vegetative inclusion in a planting of the unpatented Zoysiagrass variety 'Meyer'. 'BA-189' is either a spontaneous mutation from 'Meyer' or derived as the progeny from an outcross to an unknown pollen parent.

'BA-189' was initially propagated asexually from a single stolon. Over multiple increases at various research sites throughout Florida 'BA-189' has remained phenotypically stable and uniform. All successive asexual reproductions that were used to determine genetic stability and consistency were performed at Belle Glade, Fla. for a period of at least four years. The denomination of this new Zoysiagrass is 'BA189', but in commerce, 'BA-189' will be marketed under the synonym 'Ultimate *Zoysia*', which is its commercial designation in the United States.

The distinctness of 'BA-189' from its progenitor is based on four sets of traits including: 1) floral morphology; 2) leaf and stem morphology; 3) tissue color and pigmentation; and 4) rate of growth and cover. Measures of disease and insect resistance yielded no statistical differences.

For the purpose of registration under the 'International Convention for the Protection of New Varieties of Plants' generally known by its French acronym UPOV Convention) and noting Sections 1612 of the Manual of Patent Examination Procedures the new variety of Zoysiagrass of the present invention is named 'BA-189'.

BRIEF DESCRIPITION OF DRAWINGS

Figure 1:
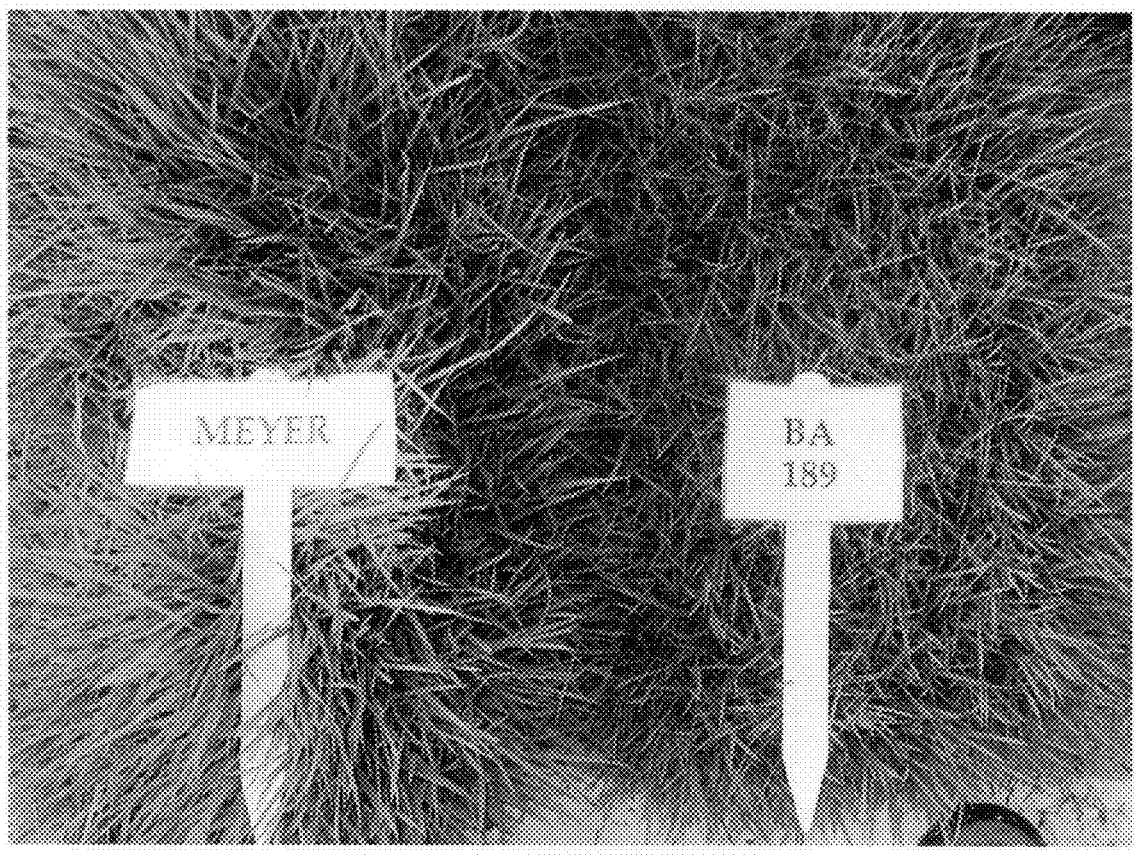

FIG. 1: A comparative photograph of 'Meyer' (left) and 'BA 189' (right). Both trays were allowed to grow side-by-side for about 3 years, under the same cultural practices and allowed to grow untrimmed for a period of more than 6 months to illustrate maximum grow out. Note the difference in leaf texture between the two genotypes.

Figure 2:
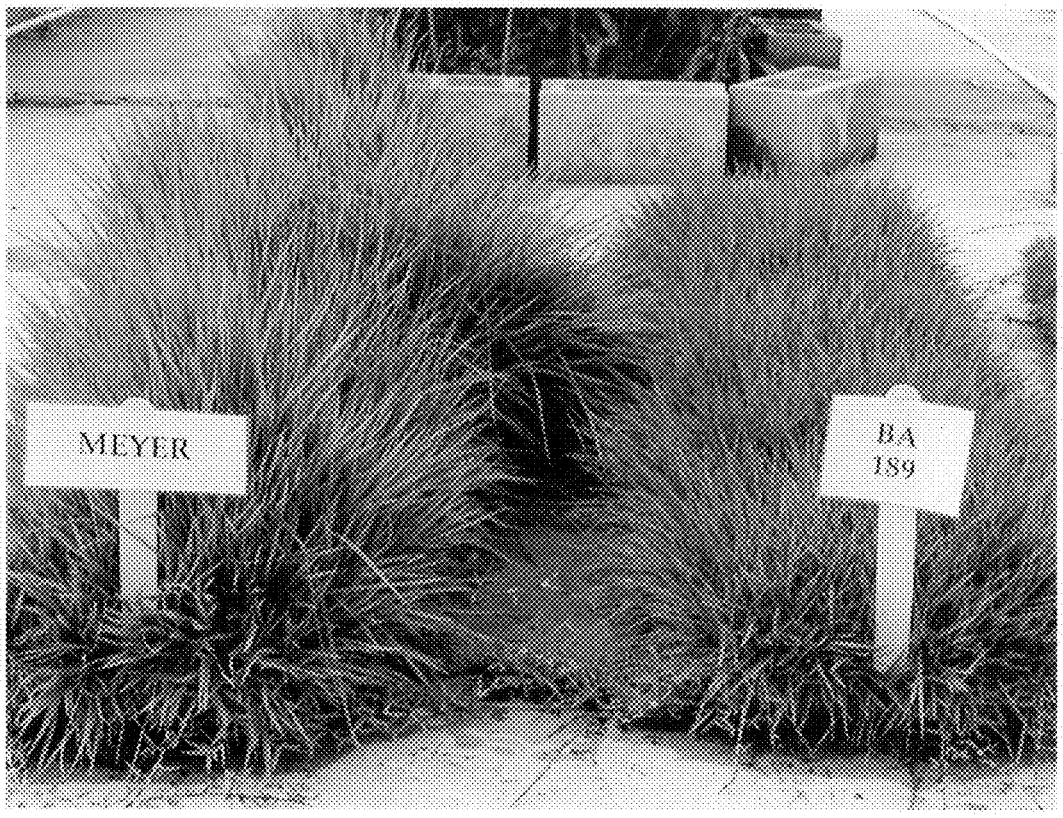

FIG. 2: A comparative photograph of 'Meyer' (left) and 'BA 189' (right). Both pots were allowed to grow side-by-side for about 4 years, under the same cultural practices, and uncut for a period of 12 months. Note the difference in terminal height.

Figure 3:
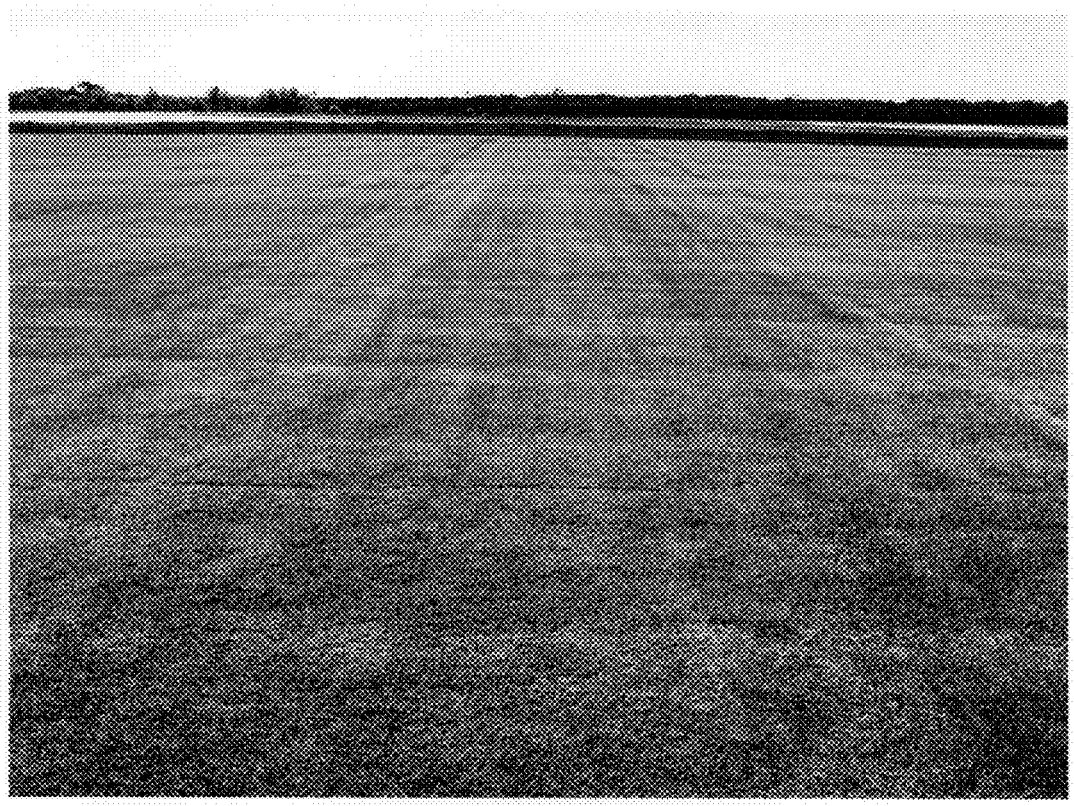

FIG. 3: A 2 year-old Breeders Block of 'BA-189' growing in Avon Park, Fla.

Figure 4:
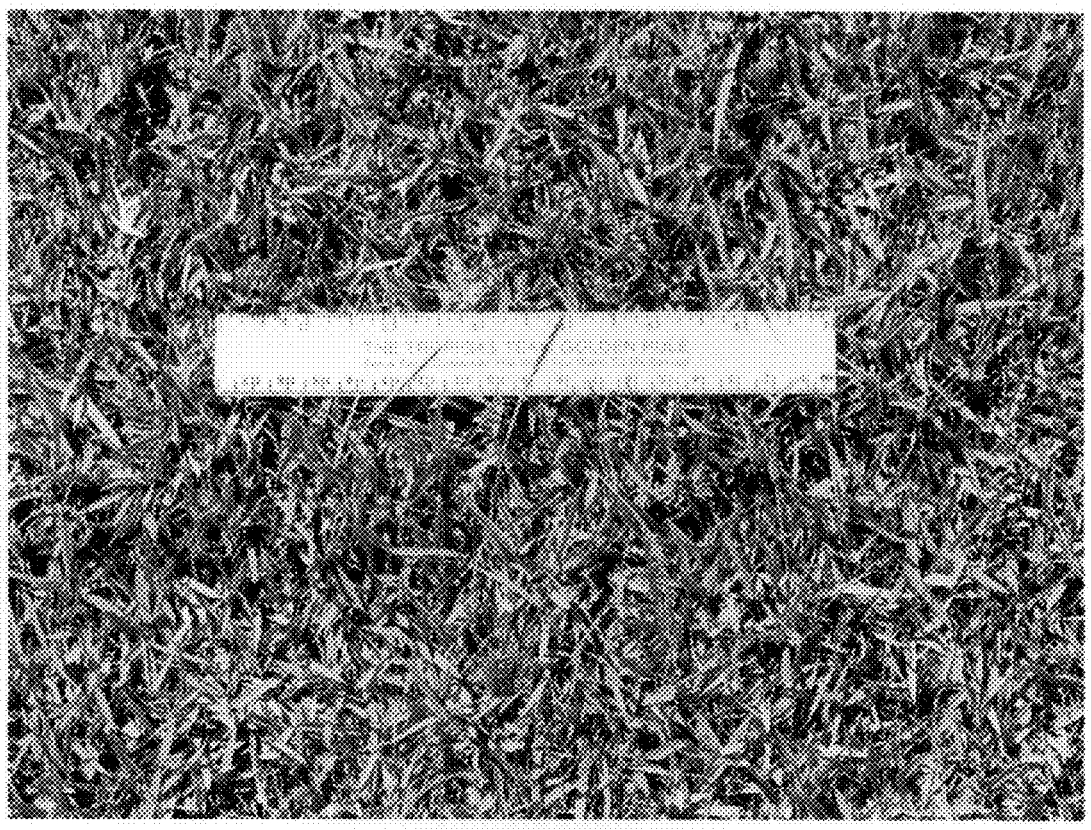

FIG. 4: A close-up photograph of 2 year-old 'BA-189', showing emerging seed heads.

Figure 5:
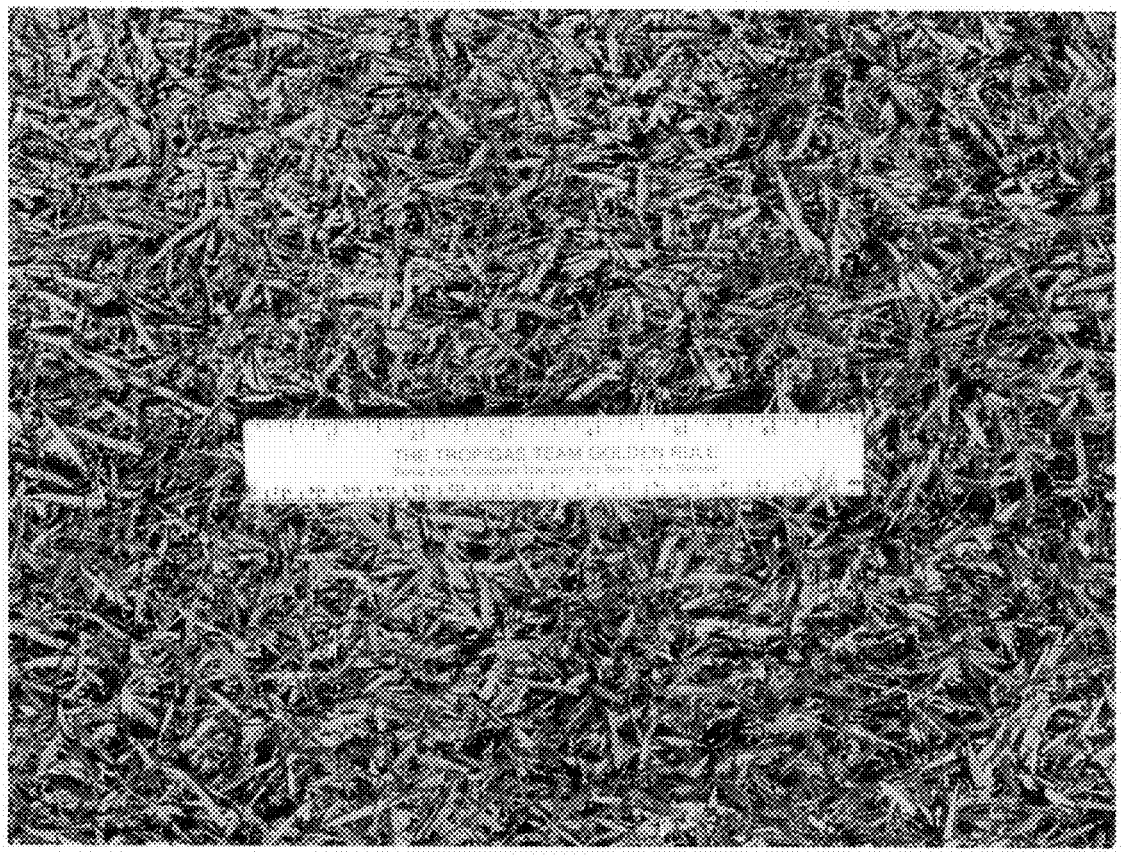

FIG. 5: A close-up photograph of 2 year-old 'BA-189' after mowing.

Figure 6:
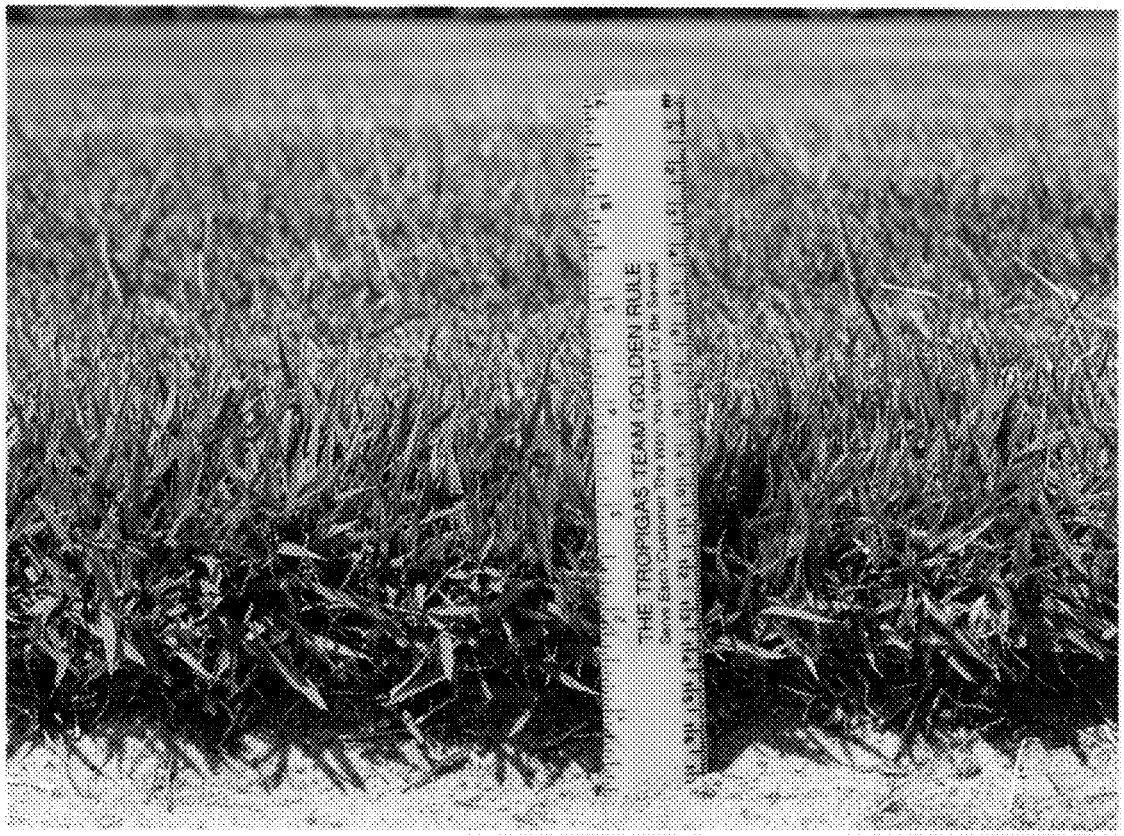

FIG. 6: A side-profile of 2 year-old 'BA-189' after a recent cutting.

DETAILED DESCRIPTION OF THE VARIETY

This new variety of Zoysiagrass is a perennial plant propagated asexually from either rhizomes, stolons, sprigs, or plugs. It is best adapted to the subtropical climates of Florida and adjacent climatic regions. 'BA-189' was tested and described under field conditions at four research sites in Florida, including Arcadia, Belle Glade, Gainesville, and Milton. Phenotypically, 'BA-189' is most similar to 'Meyer'.

The floral morphology of 'BA-189' is typical of the species *Zoysia japonica* Stued. In comparison to 'Meyer', 'BA-189' differed statistically for four of the eight measured traits (Table 1). On average 'BA-189' had a taller inflorescence, but this was not due to a significant difference in the length of the seed head or raceme. This increased height of the inflorescence is due primarily to the extended peduncle length. The overall peduncle length of 'BA-189' averaged 48.70 mm vs 34.25 for 'Meyer' (Table 1). Additionally, the glume length was also significantly longer for 'BA-189'.

Although the inflorescence of 'BA-189' is more robust, the number of inflorescences produced on a monthly basis by 'BA-189' is, on average, less than 'Meyer' (Table 4). On a monthly basis, 'BA-189' produced statistically fewer seed-heads in the months of June, July, August, September, October, November and December. No significant differences existed in January through April. These are practical advantages to having fewer seed heads produced during the growing season.

The morphology of the flag leaf is described by three metric traits that include flag leaf length, width, and sheath length. 'BA-189' differed from 'Meyer' in leaf width and sheath length (Table 2). No significant difference was detected in flag leaf length, although 'Meyer' produced a longer flag leaf.

The largest differences between 'BA-189' and 'Meyer' are expressed in leaf and stolon morphology. These traits were measured on fully expanded leaves at the fifth node below stolon meristem. 'BA-189' and 'Meyer' differed significantly for all four traits (Table 3). On average, 'Meyer' produced leaves that measured 106.9 mm long by 4.0 mm wide, while 'BA-189' produced leaves that were 83.0 mm long by 3.00 mm wide (Table 3). Roughly estimated, 'Meyer' produced leaves that individually were 70% larger that 'BA-189'. Conversely, 'BA-189' produced leaf bearing nodes every 27.4 mm compared to 36.7 mm for 'Meyer'. This theoretically allows 'BA-189' to carry up to 20% more leaf bearing nodes than 'Meyer'. The overall visual effect of these leaf and internode differences are also displayed in FIGS. 1 and 2.

Leaf color and stolon/rhizome pigment varied between the two genotypes, and was determined by the comparison of fresh leaf and stolon tissue to color swatches in the Munsell Color Chart. The adaxial surface of 'BA-189' ranged in color from 5GY (4/6 to 5/6) to 7.5GY (4/6 to 5/6), while 'Meyer' produced leaves with a less intense green color that ranged from 5GY (5/6-8 to 6/6-8). The stolons of 'Meyer' produced a pigment color that ranged up to 5RP (3/4), while the pigment in the stolons of 'BA-189' ranged up to 5RP (4/2).

Both grasses grew similarly in the warm spring and summer season, but 'BA-189' had a longer growth duration. It continued to grow and cover the plots in October and November, and began growing sooner in the winter (Table 5). The rate of coverage for 'BA-189' was statistically different than 'Meyer' in October, November, and February. Although, 'BA-189' grew somewhat in December and January, it was not significantly different from 'Meyer' in those months (Table 5). Because of this accelerated growth rate, 'BA-189' covered the plot completely in 10 months vs 11 months for 'Meyer'. The agronomic advantage of this faster growth rate is a shortened harvest interval, or depending on the harvest cycle, an earlier spring harvest. The faster growth rate for 'BA-189' was not attributed to a significant increase in either stolon number, or stolon length (Table 5). These traits were not significantly different between the two grasses over the seven months they could be measured. It is likely that the higher density of leaf bearing nodes presented earlier (Table 3) may have contributed to this faster rate of coverage.

TABLE 1

Comparison of floral traits between 'BA-189' and 'Meyer'.

| | 'BA-189' | | 'Meyer' | | |
|---|---|---|---|---|---|
| Trait | Mean | ± | Mean | ± | LSD α ≦ 0.05 |
| Overall Shoot Length[z] | 69.15 | 2.58 | 55.55 | 2.63 | 5.556 |
| Seed Head Length[y] | 20.30 | 0.65 | 21.85 | 0.98 | 1.91 (ns) |
| Seed Head Width[x] | 1.84 | 0.08 | 1.86 | 0.04 | 0.187 (ns) |
| Seed Count/Seed Head[w] | 26.90 | 1.47 | 28.25 | 1.30 | 3.10 (ns) |
| Exposed Peduncle Length[v] | 30.70 | 2.41 | 20.45 | 2.25 | 4.95 |
| Peduncle Length[u] | 48.70 | 4.47 | 34.25 | 4.47 | 5.33 |
| Glume Length[t] | 3.11 | 0.05 | 2.78 | 0.07 | 0.19 |
| Glume Width[s] | 0.99 | 0.01 | 1.00 | 0.01 | 0.06 (ns) |

[z]Overall shoot length (mm) is a measure of the total inflorescence length from the apex of the seed head to the first node on the peduncle subtending the raceme.
[y]Seed Head Length (mm) is measured from the apex of the seed head to the top of the peduncle or base of the raceme.
[x]Seed Head Width (mm) is measured at the broadest part of the seed head.
[w]Seed Count/Seed Head is the average number of seeds per head or raceme.
[v]Exposed Peduncle Length (mm) is the average length of the peduncle not covered by the flag leaf sheath.
[u]Peduncle Length (mm) is the average peduncle length measured from the base of the seed head to the top node.
[t]Glume Length (mm) is a measure of the average glume length on the seed located at the midpoint along the seed head.
[s]Glume Width (mm) is measured at the widest part of the glume.

TABLE 2

Comparison of flag leaf traits between 'BA-189' and 'Meyer'.

| | 'BA-189' | | 'Meyer' | | |
|---|---|---|---|---|---|
| Trait (mm) | Mean | ± | Mean | ± | LSD α ≦ 0.05 |
| Flag Leaf Length | 6.93 | 0.51 | 7.68 | 0.59 | 1.87 (ns) |
| Flag Leaf Width[z] | 0.86 | 0.03 | 0.97 | 0.35 | 0.08 |
| Flag Leaf Sheath Length | 16.40 | 1.09 | 12.90 | 0.73 | 2.33 |

[z]Flag Leaf width is measured at the widest part of the leaf.

TABLE 3

Comparison of leaf morphology between 'BA-189' and 'Meyer'.

| | 'BA-189' | | 'Meyer' | | |
|---|---|---|---|---|---|
| Trait (mm) | Mean | ± | Mean | ± | LSD α ≦ 0.05 |
| Leaf Length | 83.02 | 3.79 | 106.88 | 3.09 | 8.34 |
| Leaf Width[z] | 3.00 | 0.10 | 4.02 | 0.11 | 0.25 |
| Internode Length | 27.37 | 0.92 | 32.68 | 1.12 | 2.29 |
| Internode Width[y] | 1.73 | 0.05 | 2.07 | 0.08 | 0.18 |

[z]Leaf Width is measured at the widest point of the leaf.
[y]Internode Width is measured at the widest point on the internode.

TABLE 4

Comparison of the average monthly seed head production for 'BA-189' and 'Meyer'.

| | Month | | | |
|---|---|---|---|---|
| Seed Head[z] | APRIL | MAY | JUNE | JULY |
| 'BA-189' | 0 | 0 | 0.5 ± 0.5 | 0 |
| 'Meyer' | 0 | 0 | 10.75 ± 1.49 | 25.15 ± 3.68 |

TABLE 4-continued

Comparison of the average monthly seed head production for 'BA-189' and 'Meyer'.

| Seed Head[z] | Month | | | |
|---|---|---|---|---|
| | AUGUST | SEPTEMBER | OCTOBER | NOVEMBER |
| 'BA-189' | 0 | 5.57 ± 1.38 | 12.50 ± 4.97 | 16.25 ± 4.27 |
| 'Meyer' | 29.75 ± 8.91 | 39.75 ± 12.47 | 38.50 ± 12.14 | 29.50 ± 8.26 |

| Seed Head[z] | Month | | |
|---|---|---|---|
| | DECEMBER | JANUARY | FEBRUARY |
| 'BA-189' | 14.25 ± 7.82 | 11.25 ± 4.89 | 8.25 ± 2.78 |
| 'Meyer' | 24.00 ± 6.65 | 18.50 ± 4.99 | 12.75 ± 4.50 |

| Seed Head[z] | Month | |
|---|---|---|
| | MARCH | APRIL |
| 'BA-189' | 7.00 ± 2.20 | 3.50 ± 1.27 |
| 'Meyer' | 6.50 ± 3.33 | 7.75 ± 4.35 |

[z]Seed Head Count is measured as mean ± standard error on a 8.0 $dm^2$ plot.

TABLE 5

Comparison of the average percentage cover, stolon/rhizome count and stolon/rhizome length measured on a monthly basis.

| | Month | | | |
|---|---|---|---|---|
| | APRIL | MAY | JUNE | JULY |
| Cover[(z)] | | | | |
| 'BA-189' | 0 | 5.0 ± 0.0 | 28.75 ± 2.39 | 57.75 ± 3.57 |
| 'Meyer' | 0 | 6.25 ± 1.25 | 40.0 ± 2.04 | 55.00 ± 5.40 |
| Stolon Number[(y)] | | | | |
| 'BA-189' | 0 | 0 | 4.00 ± 0.71 | 10.50 ± 1.94 |
| 'Meyer' | 0 | 0 | 4.7 ± 0.63 | 7.75 ± 1.60 |
| Stolon Length[(x)] | | | | |
| 'BA-189' | 0 | 0 | 3.25 ± 0.95 | 3.00 ± 0.41 |
| 'Meyer' | 0 | 0 | 4.50 ± 0.65 | 3.75 ± 0.25 |

| | Month | | | |
|---|---|---|---|---|
| | AUGUST | SEPTEMBER | OCTOBER | NOVEMBER |
| Cover[(z)] | | | | |
| 'BA-189' | 56.25 ± 10.48 | 71.25 ± 1.25 | 86.25 ± 4.73 | 87.50 ± 4.33 |
| 'Meyer' | 58.75 ± 6.57 | 65.00 ± 8.92 | 77.50 ± 4.79 | 81.25 ± 4.27 |
| Stolon Number[(y)] | | | | |
| 'BA-189' | 9.25 ± 1.55 | 9.25 ± 1.55 | 10.00 ± 1.22 | — |
| 'Meyer' | 12.50 ± 0.29 | 13.25 ± 0.95 | 11.25 ± 2.17 | — |
| Stolon Length[(x)] | | | | |
| 'BA-189' | 4.75 ± 1.65 | 8.50 ± 1.26 | 8.25 ± 1.44 | — |
| 'Meyer' | 4.75 ± 0.48 | 8.25 ± 1.03 | 8.25 ± 1.03 | — |

TABLE 5-continued

Comparison of the average percentage cover, stolon/rhizome count and stolon/rhizome length measured on a monthly basis.

| | Month | | |
|---|---|---|---|
| | DECEMBER | JANUARY | FEBRUARY |
| Cover[(z)] | | | |
| 'BA-189' | 96.25 ± 2.39 | 97.50 ± 1.44 | 100.00 ± 0 |
| 'Meyer' | 91.25 ± 7.18 | 91.25 ± 7.18 | 93.75 ± 6.25 |
| Stolon Number[(y)] | | | |
| 'BA-189' | — | — | — |
| 'Meyer' | — | — | — |
| Stolon Length[(x)] | | | |
| 'BA-189' | — | — | — |
| 'Meyer' | — | — | — |

| | Month | |
|---|---|---|
| | MARCH | APRIL |
| Cover[(z)] | | |
| 'BA-189' | 100.00 ± 0 | 100.00 ± 0 |
| 'Meyer' | 100.00 ± 0 | 100.00 ± 0 |
| Stolon Number[(y)] | | |
| 'BA-189' | — | — |
| 'Meyer' | — | — |
| Stolon Length[(x)] | | |
| 'BA-189' | — | — |
| 'Meyer' | — | — |

[(z)]Cover is measured as the average cumulative percentage of cover over a prescribed plot area.
[(y)]Stolon Number is a count of stolons/rhizomes radiating from a central plug over a prescribed plot area.
[(x)]Stolon Length is an average measure in cm of the stolons/rhizomes.

REFERENCES

1952. Release of 'Meyer' *Zoysia* to State Experiment Stations. USGA Journal and Turf Management. 5:26-27.

1977. Munsell Color Charts for Plant Tissue 2$^{nd}$ Ed.) Munsell Color, New Windsor, N.Y. 20p.

Beard, James B. 1973. Turfgrass: Science and Culture. Prentice Hall, Englewood Cliffs, N.J. 658p.

Forbes, I., B. P. Robinson and J. M. Latham. 1955. 'Emerald' *Zoysia*—an Improved Hybrid Lawn Grass for the South. USGA Journal and Turf Management 8:23:26.

We claim:

1. A new and distinct type of Zoysiagrass plant substantially described and illustrated herein.

* * * * *